United States Patent

Aya et al.

[11] 3,978,107
[45] Aug. 31, 1976

[54] NOVEL CYCLOHEXYL CARBAMATES AND HERBICIDAL AND ACARICIDAL COMPOSITIONS

[75] Inventors: Masahiro Aya; Akio Kudamatsu; Masao Miyamoto; Nobuo Fukazawa; Shigeki Osuga, all of Tokyo, Japan

[73] Assignee: Bayer Aktiengesellschaft, Leverkusen, Germany

[22] Filed: May 10, 1971

[21] Appl. No.: 142,026

[30] Foreign Application Priority Data
May 9, 1970  Japan............................. 45-39186

[52] U.S. Cl............................. 260/455 A; 71/100; 424/300
[51] Int. Cl.² .................................. C07C 155/03
[58] Field of Search ........... 260/455 A; 71/100, 101

[56] References Cited
UNITED STATES PATENTS

| | | | |
|---|---|---|---|
| 2,992,091 | 7/1961 | Harman et al. | 71/100 |
| 3,344,134 | 9/1967 | D'Amico | 260/455 A |
| 3,450,745 | 6/1969 | Payne, Jr. et al. | 260/455 A |
| 3,510,290 | 5/1970 | Doyle, Jr. | 71/90 |
| 3,532,488 | 10/1970 | Husted et al. | 260/455 A |
| 3,679,726 | 7/1972 | Kudamatsu | 260/455 A |

FOREIGN PATENTS OR APPLICATIONS
882,110   11/1961   United Kingdom............. 260/455 A Primary Examiner—Glennon H. Hollrah
Attorney, Agent, or Firm—Burgess, Dinklage & Sprung

[57] ABSTRACT

Certain new cyclohexyl carbamates of the formula:

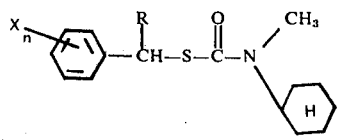

wherein
X is hydrogen, halogen, lower alkyl or lower alkoxy,
R is hydrogen or methyl, and
n is 1, 2, or 3,
are outstandingly effective herbicides and acaricides and have found particular applicability in selectively combating weeds growing in paddy fields.

3 Claims, No Drawings

NOVEL CYCLOHEXYL CARBAMATES AND HERBICIDAL AND ACARICIDAL COMPOSITIONS

The present invention relates to certain new cyclohexyl carbamate compounds, to herbicidal and acaricidal compositions containing them, and to their use as herbicides and acaricides.

For the control of barnyard grass, a weed growing in paddy fields, pentachlorophenol (PCP) has hitherto been used; however, this chemical is not only extremely irritating to the mucous membranes of human skin and difficult to formulate, but also very poisonous to fish. Therefore the time and scope of its usage are limited. For the controlling of spikerush, a weed growing in the same conditions as barnyard grass, 2-methyl-4-chlorophenoxy-acetic acid (MCP) is used, but MCP is not very effective for that purpose.

Among other herbicides, French Patent No. 1328112 indicates that benzyl-N,N-di-alkylthiolcarbamic acid esters have a herbicidal activity and Japanese Patent Publication No. 29024/68 indicates that halogen-substituted benzylthiolcarbamic acid esters exhibit a herbicidal activity.

It has now surprisingly been discovered that certain novel substituted (or unsubstituted) benzyl or α-methyl substituted (or unsubstituted) benzyl N-methyl-N-cyclohexylcarbamates of the general formula (I) are excellent selective herbicides and are suitable for controlling weeds growing in paddy fields, e.g., Echinochloa (barnyard grass), Eleochalis acicularis (spikerush) and broad-leaved weeds without significant injury to the rice plant.

These compounds have the following general formula:

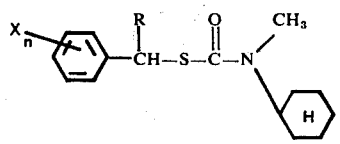

(I)

wherein
X is hydrogen, halogen, lower alkyl or lower alkoxy,
R is hydrogen or methyl, and
n is 1, 2, or 3,
(when n is 2 or 3, the various X radicals may be the same or different).

The compounds of the present invention are characterized by strong herbicidal activity when used not only before the germination of barnyard grass but also at the 1 to 3 leaf stage under irrigation conditions, and by less phytotoxicity against rice plants in comparison with the afore-said conventional benzylthiolcarbamate. This is a very important feature since many other herbicides now on the market are effective against barnyard grass only in the pre- or the immediate post-emergence period. Moreover, because of their lower phytotoxicity against rice plants, the compounds of the present invention can be used to control weeds in paddy fields and yet save much labor in cultivation, when applied a week or two after transplantation, a stage for which no proper controlling method is available at present.

The compounds of the present invention have strong herbicidal activity when absorbed through roots, and they can be used as non-selective or as selective herbicides against weeds (including those in paddy fields), especially during the preparation of the soil before germination. Furthermore, the compounds of this invention are effective as acaricides, and especially against carmine mites. When used as acaricides on plants they also show only little phytotoxicity. Accordingly the compounds of this invention may be used not only as herbicides but also as acaricides.

The invention also provides a process for the production of a compound of formla (I) in which
a. a benzylmercaptan of the general formula

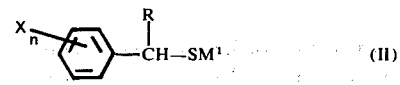

(II)

is reacted with N-methyl-N-cyclohexyl-carbamoyl chloride of the formula

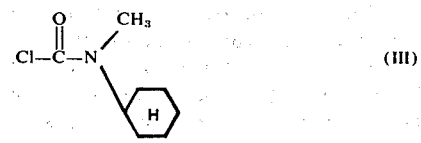

(III)

or b. a benzylthio-carbonyl chloride of the general formula

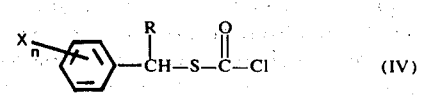

(IV)

is reacted with N-methyl-N-cyclohexylamine of the formula

(V)

or c. a benzyl halide of the general formula

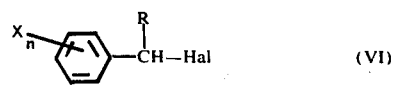

(VI)

is reacted with N-methyl-N-cyclohexylamine of the formula (V) and COS and an alkali of the formula $M^2$—OH (VII)
X, R and n having the same meanings as in formula (I),
$M^1$ being hydrogen or an alkali metal,
Hal being halogen, and
$M^2$ being alkali metal.

Process variant (a) is illustrated by the following reaction scheme,

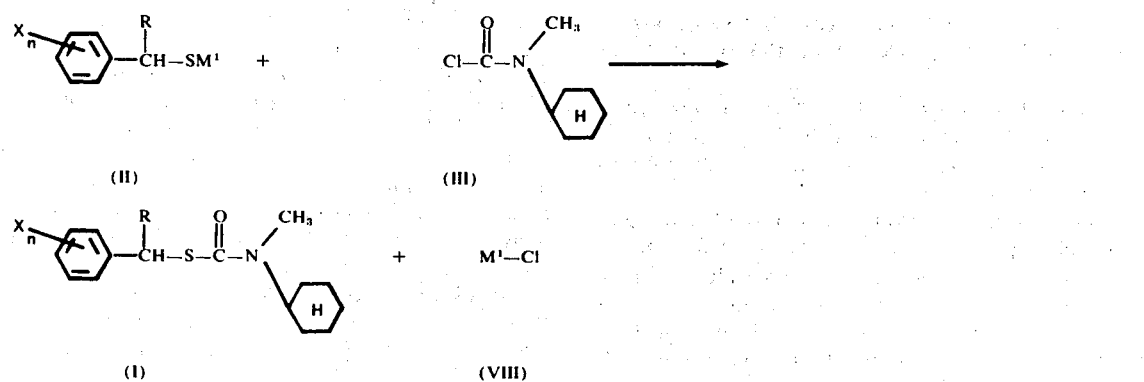

(II)                        (III)

(I)                        (VIII)

Examples of benzyl mercaptans of formula (II) include benzyl-, 2-(3- or 4-)chlorobenzyl-, 3,4-(or 2,4-)dichlorobenzyl-, 4-methyl(or iso-propyl-)benzyl-, 2-chloro-5-bromobenzyl-, 3,4-(or 2,5-)dimethylbenzyl-, 2,4,5-(or 2,4,6-)trimethylbenzyl-, 4-methoxybenzyl-, 3-methyl-4-methoxy-(ethoxy- or iso-propoxy) benzyl-, 3-methoxy-5-chlorobenzyl-, α-methylbenzyl-, α-methyl-2-(or 4-)chlorobenzyl-, and α-methyl-4-methyl(or methoxy)benzylmercaptan and their alkali metal salts.

The above-mentioned reaction is preferably performed in the presence of an inert organic solvent. For this purpose, aliphatic or aromatic hydrocarbons (which may be halogenated), such as benzine, methylene chloride, chloroform, carbon tetrachloride, benzene, chlorobenzene, toluene or xylene; ethers such as diethylether, dibutulether, dioxan or tetrahydrofuran; low-boiling point alcohols such as methanol, ethanol or isopropanol; and ketones such as acetone, methylethylketone, methylisopropylketone or methylisobutylketone, are suitable. Lower aliphatic nitriles such as acetonitrile or propionitrile can also be used.

This reaction can also be carried out in the presence of an acid binding agent, if necessary. For this purpose, carbonates and bicarbonates of alkali metals, such as sodium bicarbonate, potassium carbonate or sodium carbonate, alcoholates of alkali metal such as methylate or ethylate or potassium or sodium, and aliphatic, aromatic or heterocyclic tertiary bases, such as triethylamine, diethylaniline and pyridine, can be used.

Process variant b is illustrated by the following reaction scheme:

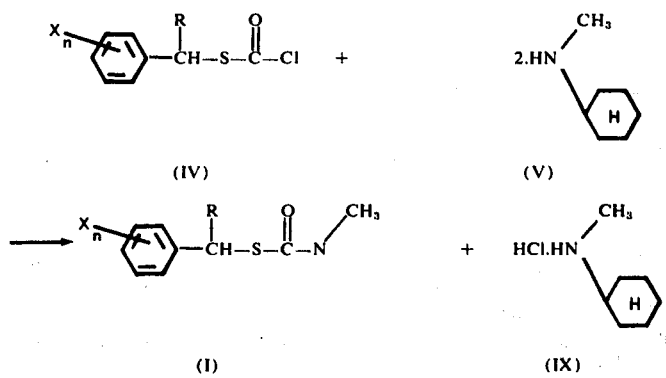

(IV)                        (V)

(I)                        (IX)

Examples of benzylthio-carbonyl chloride of the formula (IV) include benzyl-, 2-(3- or 4-)chlorobenzyl-, 3,4-(or 2,4-)dichlorobenzyl-, 4-methyl(or iso-propyl-)benzyl-, 2-chloro-5-bromobenzyl-, 3,4-(or 2,5-)dimethyl-benzyl-, 2,4,5-(or 2,4,6-) trimethylbenzyl-, 4-methoxybenzyl-, 3-methyl-4-methoxy-(ethoxy- or iso-propoxy)benzyl-, 3-methoxy-5-chlorobenzyl-, α-methylbenzyl-, α-methyl-2-(or 4-)chlorobenzyl-, and α-methyl-4-methyl (or methoxy)benzyl-thiocarbonyl-chloride. This reaction can also be carried out in the presence of an inert organic solvent as mentioned above for variant (a).

Process variant (c) is illustrated by the following reaction scheme:

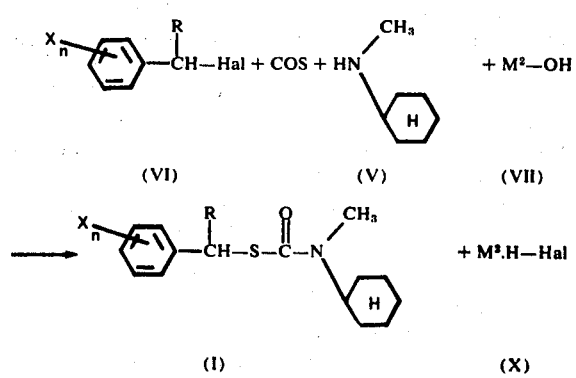

(VI)          (V)          (VII)

(I)                        (X)

This reaction is preferably carried out in the presence of an inert organic solvent as mentioned above for process variant (a).

The preparation of the compounds of the invention is illustrated by the following Examples 1 and 2.

EXAMPLE 1

Preparation of benzyl-N-methyl-N-cyclohexylthiolcarbamate

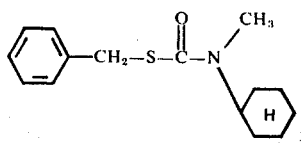

14.6 g (0.1 mol) of the sodium salt of benzylmercaptan were mixed with 150 ml of acetone. Then, while the mixture was being stirred, 17.6 g (0.1 mol) of N-methyl-N-cyclohexylcarbamoylchloride were gradually added dropwise thereto at room temperature. After the dropping was over, the reaction was completed by further stirring for 2 - 3 hours. The acetone was distilled off and 300 ml of benzene was added to the extract. The benzene layer was taken off and washed with 1% hydrochloric acid, 1% sodium hydroxide and water, and was thereafter dried over anhydrous sodium sulfate. After continuing the distillation under reduced pressure after distilling off the benzene, 24.9 g of benzyl-N-methyl-N-cyclohexylthiolcarbamate were obtained.

Yield: 90.9%. b.p. : 157° – 160°C/0.5 mmHg. The index of refraction $n_D^{20}$ was 1.5644.

EXAMPLE 2

Preparation of α-methyl--chlorobenzyl-N-methyl-N-cyclohexylthiolcarbamate -chlorobenzyl-N-methyl-N-cyclohexylthiocarbamate

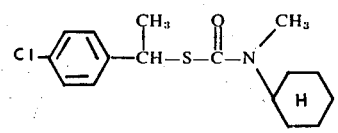

23.5 g (0.1 mol) of α-methyl-4-chlorobenzylthiocarbonylchloride was dissolved in 200 ml of acetone. The solution was cooled to 0 - 5°C. 22.6 g (0.2 mol) of N-methyl-N-cyclohexylamine dissolved in 100 ml of acetone were added dropwise to the solution with stirring. The mixture was reacted for one hour after completion of the addition, and was allowed to stand at room temperature for 12 hours. From the reacted mixture, the precipitated amine salt was filtered off. The acetone layer, the filtrate, was washed with 1% sodium hydroxide, 1% hydrochloric acid and water, and then it was dried over anhydrous sodium sulfate. 28.2 g of α-methyl-4-chlorobenzyl-N-methyl-N-cyclohexylthiolcarbamate were obtained under reduced pressure distillation after distilled off the acetone.

Yield : 90.4%. b.p. : 170° – 173°C/0.2 mmHg. The index of refraction $n_D^{20}$ was 1.5671.

The following table lists representative compounds of the present invention which were prepared according to methods analogous to those of the above Examples (the compounds of the above Examples are included in the Table I.

Table I

| Compound | Structural Formula | Chemical Name | Physical Property b.p. °C/mmHg (the index of refraction $n_D^{20}$) [m.p.°C] |
|---|---|---|---|
| (1) | | Benzyl-N-methyl-N-cyclohexylthiolcarbamate | 157 – 160/0.5 (1.5644) |
| (2) | | 2-Chlorobenzyl-N-methyl-N-cyclohexylthiolcarbamate | 174 – 176/0.5 (1.5766) |
| (3) | | 4-Chlorobenzyl-N-methyl-N-cyclohexylthiolcarbamate | 165 – 170/0.3 (1.5748) |
| (4) | | 3,4-Dichlorobenzyl-N-methyl-N-cyclohexylthiolcarbamate | 195 – 198/0.2 (1.5849) |

Table I-continued

| Compound | Chemical Name | Physical Property b.p. °C/mmHg (the index of refraction $n_D^{20}$) [m.p.°C] |
|---|---|---|
| (5) | 2-Chloro-5-bromobenzyl-N-methyl-N-cyclohexylthiol-carbamate | 177 – 180/0.2 (1.5941) |
| (6) | 4-Methylbenzyl-N-methyl-N-cyclohexylthiolcarbamate | [50 – 51] |
| (7) | 4-Ethylbenzyl-N-methyl-N-cyclohexylthiolcarbamate | 180 – 184/0.2 (1.5608) |
| (8) | 4-Iso-propylbenzyl-N-methyl-N-cyclohexylthiolcarbamate | 178 – 184/0.2 (1.5559) |
| (9) | 3,4-Dimethylbenzyl-N-methyl-N-cyclohexylthiol-carbamate | [60 – 62] |
| (10) | 2,5-Dimethylbenzyl-N-methyl-N-cyclohexylthiol-carbamate | 165 – 170/0.1 |
| (11) | 2,4,5-Trimethylbenzyl-N-methyl-N-cyclohexylthiol-carbamate | 178 – 183/0.3 (1.5654) |
| (12) | 4-Methoxybenzyl-N-methyl-N-cyclohexylthiolcarbamate | 173 – 177/0.2 (1.5659) |
| (13) | 3-Methyl-4-methoxybenzyl-N-methyl-N-cyclohexylthiol-carbamate | [57 – 58] |

Table I-continued

| Compound | Chemical Name | Physical Property b.p. °C/mmHg (the index of refraction $n_D^{20}$) [m.p.°C] |
|---|---|---|
| (14) | 3-Methyl-4-ethoxybenzyl-N-methyl-N-cyclohexylthiol-carbamate | [51 – 52] |
| (15) | 3-Methyl-4-iso-propoxybenzyl-N-methyl-N-cyclohexylthiol-carbamate | 178 – 179/0.2 (1.5520) |
| (16) | 2-Methoxy-5-methylbenzyl-N-methyl-N-cyclohexylthiol-carbamate | 173 – 176/0.2 (1.5650) |
| (17) | 3-Chloro-4-methoxybenzyl-N-methyl-N-cyclohexylthiol-carbamate | 175 – 180/0.2 (1.5766) |
| (18) | 3-Chloro-4-ethoxybenzyl-N-methyl-N-cyclohexylthiol-carbamate | 189 – 193/0.4 (1.5689) |
| (19) | 3-Chloro-4-iso-propoxybenzyl-N-methyl-N-cyclohexylthiol-carbamate | 180 – 185/0.3 (1.5581) |
| (20) | 2-Methoxy-5-chlorobenzyl-N-methyl-n-cyclohexylthiol-carbamate | 185 – 188/0.4 (1.5749) |
| (21) | α-Methylbenzyl-N-methyl-N-cyclohexylthiolcarbamate | 170 – 173/0.2 (1.5632) |

Table I-continued

| Compound | Chemical Name | Physical Property b.p. °C/mmHg (the index of refraction $n_D^{20}$) [m.p.°C] |
|---|---|---|
| (22) | α-Methyl-2-chlorobenzyl-N-methyl-N-cyclohexylthiol-carbamate | 185 – 189/0.2 (1.5699) |
| (23) | α-Methyl-4-chlorobenzyl-N-methyl-N-cyclohexylthiol-carbamate | 170 – 173/0.2 (1.5671) |
| (24) | α-Methyl-4-methylbenzyl-N-methyl-N-cyclohexylthiol-carbamate | 160 – 165/0.3 (1.5564) |
| (25) | α-Methyl-4-methoxybenzyl-N-methyl-N-cyclohexylthiol-carbamate | 175 – 180/0.4 (1.5621) |

The compounds of the present invention are superior in weed-controlling activity to many known compounds having similar structures.

The compounds can have either a total herbicidal effect or a selective herbicidal effect, depending mainly on the amount used. Larger amounts, for example 5 to 40 kg of active compound per hectare, generally have a total herbicidal effect, whereas small amounts, for example 1.25 to 5 kg of active compound per hectare, generally have a selective effect.

The compounds according to the present invention can be effectively used as germination-controlling agents especially weed-controlling agent.

The term weed used herein is intended broadly to cover most plants growing where they are not desired.

The compounds according to the present invention have good activity against the following plants, and exhibit excellent selective weed-killing or withering effects when used in appropriate amounts (for example 1.25 to 5 kg per hectare), and can be especially useful as herbicides in the cultivation of crops indicated by an asterisk in the following list.

| Plant name | Latin name |
|---|---|
| Dicotyledons | |
| Mustard | Sinapis |
| Rape | Lepidium |
| Catch weed | Galium |
| Chickweed | Stellaria |
| Sweet false | Matricaria |
| French weed | Galinsoga |
| Goosefoot | Chenopodium |
| Nettle | Urtica |
| Groundsel | Senecio |
| Tampala | Amaranthus |
| Purslane | Portulaca |
| cotton | *Gossypium |
| Carrot | *Daucus |
| Pulse | *Phaseolus |
| Potato | *Solanum |
| Coffee | *Coffea |
| Beet | *Beta |
| Cabbage | *Brassica |
| Spinach | *Spinacia |
| Monocotyledons | |
| Timothy | Phleum |
| Eragrostis niwahokori Honda | Poe |
| Festuca parvigluma | Festuca |
| Finger-grass | Digitaria |
| Goose grass | Eleusine |
| Nit 70 | |
| Foxtail | Setaria |
| Ray grass | Bromus |
| Barn yard grass | Echinochlora |
| Maize | *Zea |
| Rice plant | *Oryza |
| Oats | *Avena |
| Barley | *Hordeum |
| Wheat | *Tritium |
| Millet | *Panicum |
| Sugar cane | *Saccharum |

The species of the above plants are considered to be typical examples of the genus identified by the Latin name. The applicability of the active compounds according to the present invention is, of course, not limited to these plants and they are effective for other analogous plants.

The active compounds according to the present invention can be utilized, if desired, in the form of the usual preparations, compositions or formulations with conventional inert (i.e. plant compatible or herbicidally inert) pesticide diluents or carriers.

These may be prepared in known manner, for example by mixing the active compounds with extenders, that is, liquid or solid or gaseous diluents and/or carriers, optionally with the use of conventional pesticide adjuvants, that is, emulsifying agents and/or dispersing agents and/or adhesive agents. In the case of the use of water as an extender, organic solvents and, emulsifying agent can, for example, also be used as auxiliary solvents.

As liquid diluents or carriers, there are preferably used aromatic hydrocarbons, such as xylenes, toluene, benzene, dimethyl naphthalene or aromatic naphthas haloganated (chlorinated) aromatic or aliphatic hydrocarbons, such as chlorobenzenes, chloromethylene, chloroethylene or carbon tetrachloride, aliphatic hydrocarbons, such as cyclohexane or paraffins (for example petroleum fractions), alcohols, such as methanol or butanol, ketones such as acetone, methyl ethyl ketone or cycohexanone, amines such as ethanol amine, ethers such as glycol monomethyl ether, strongly polar solvents, such as dimethyl formamide, dimethyl sulfoxide or acetonitrile, as well as water.

As solid diluents or carriers, there are preferably used ground natural minerals, such as clays, talc, chalk, i.e. calcium carbonate, attapulgite, montmorillonite, diatomaceous earth or pumice or ground synthetic minerals, such as highly-dispersed silicic acid, alumina or silicates.

As gaseous diluents or carriers there may be used aerosol propellants which are gaseous at normal temperatures and pressures, such a freon.

Preferred examples of adjuvants (diluents or carriers assistants) include non-ionic cationic and anionic emulsifiers, such as polyoxyethylene-fatty acid esters, polyoxyethylene-fatty alcohol ethers, for example alkylarylpolyglycol ethers, alkyl sulfonates and aryl sulfonates; and preferred examples of dispersing or adhesive agents include lignin, sulfite waste liquors and methyl cellulose.

The compounds of the present invention can be used, if desired, together with other agricultural chemicals, for example insecticides, nematocides, fungicides (including antibiotics), herbicides, plant growth-regulators or fertilizers.

The herbicidal, and acaricidal composition according to the present invention generally contains 0.1 to 95 per cent by weight, preferably 0.5 to 90% by weight, of the active compound. However, the content of active ingredients may be varied in accordance with the formulation and the applying method, the purpose, the period of application, the place of application and other circumstances.

The compounds may be formulated in any of the usual ways in the field of agricultural chemicals, for example solutions, emulsions, emulsion concentrates, wettable powders, aqueous solutions, oil formulations, aerosols, pastes, fumigants, dusting powders, coating granules, tablets, granules, pellets and the like.

The compounds may be applied to the pest or its habitat in any of the usual ways, for example, by scattering, spraying, atomizing, misting, dusting, mixing, fumigating, injecting or powder-coating methods.

Furthermore, the application can be effected by the so-called "ultra-low-volume" method. In this method it may be possible to use 95% to 100% of the active compound.

In use, the content of the active ingredient in the ready-to-use preparation can be varied over a broad range according to circumstances above. However, it may generally be preferable to use a range from 0.001 to 20% by weight, especially 0.005 to 15.0% by weight.

Also, the amount of active compound applied per unit, area is usually about 15 to 2000 grams, preferably 40 to 1000 grams of active compound per 10 ares. However, in special cases it may be possible to use or more less sometimes such variations may be required.

The invention therefore provides a herbicidal or acaricidal composition containing as active ingredient a compound according to the invention in admixture with a solid diluent or carrier or in admixture with a liquid diluent or carrier, if desired, containing adjuvant.

The invention also provides a method of combating weeds, acarids or fungi which comprises applying to these pests or a habitat thereof a compound according to the invention alone or in the form of a composition containing as active ingredient a compound according to the invention in admixture with a solid or liquid diluent or carrier or adjuvant.

The invention also provides crops protected from damage by seeds or acarids by being grown in areas in which, immediately prior to and/or during the time of the growing, a compound according to the invention was applied alone or in admixture with a solid or liquid diluent or carrier. It will be seen that the usual methods of providing harvested crops may be improved by the present invention.

The invention is illustrated by the following Examples. In all the Examples, the numbers of the compounds correspond to those in Table 1, infra.

The following Examples (i) through (iv) are illustrative of conventional formulation techniques used in preparing pesticidal compositions of the instant compounds and Examples (A) through (C) illustrate the acaricidal activity of compounds of this invention.

Example (i)

15 parts of compound (3), 80 parts of a mixture of talc and clay and 5 parts of the emulsifier Runnox (Trade Name, product of Toho Chemical Ind. Corp.) were mix-crushed to give a wettable powder. It is diluted with water for actual application. [talc and clay (3:1); The term "parts" used in the Example (i) to (iv) means "weight".]

Example (ii)

30 parts of compound (1), 30 parts of xylol, 30 parts of Kawakazol (Produced by Kawasaki Kasei K. K.) and 10 parts of the emulsifier Sorpol (Trade Mark) were mixed to give an emulsion concentrate. It was applied after being diluted with water. (Kawakazol: aliphatic hydrocarbons with high boiling point ; Sorpol: polyoxyethylenealkylarylether)

Example (iii)

To a mixture of 10 parts of compound (15), 10 parts of bentonite, 78 parts of clay and 2 parts of lignin sulfate there were added 25 parts of water. The mixture was well kneaded and cut into fine particles (20–40 mesh) by means of an extrusion type granulating machining and was dried at 40° to 50°C. In use, the granular was directly applied.

Example (iv)

2 parts of compound (17) of the table and 98 parts of a mixture of talc and clay were comminuted and mixed to form a powder for application.

EXAMPLE A

Pre-emergence soil-treating test for weeds in paddy field under irrigation:
Solvent: 5 parts by weight of acetone
Emulsifier: 1 part by weight of benzyloxypolyglycol ether.

The active compound was incorporated into an emulsifiable concentrates by mixing 1 part by weight thereof with the stated amounts of the said solvent and emulsifier.

The preparation thus obtained was diluted with water.

Test method

A 1/5000 are Wagner pot was charged with paddy field soil, and a rice plant seedling (variety: Kinmaze) during the 3rd to the 4th leaf stage was transplanted into the pot.

After rooting of the seedling, seeds of Panicum crusgalli and a broad-leaved weed were sown, and Eleocharis acicularis var. longiseta was transplanted into the pot.

The said preparation of active compound was applied into the pot at a dosage of 500, 250 or 125 grams of active compound per 10 ares. The damage degrees of the weeds to be tested after four weeks were evaluated on a scale from 0 to 5, the scale values having the following meanings. The degree of phytotoxicity was also determined in accordance with the second scale below.

Degree of damage

| | | | |
|---|---|---|---|
| 5: | Weed-killing rate as compared with untreated plot | over 95 % | (withering) |
| 4: | " | over 80 % | |
| 3: | " | over 50 % | |
| 2: | " | over 30 % | |
| 1: | " | over 10 % | |
| 0: | " | below 10 % | (not effective) |

Degree of phytotoxicity

| | | | |
|---|---|---|---|
| 5: | Phytotoxicity rate as compared with untreated plot | over 90 % | (mortal damage) |
| 4: | " | over 50 % | |
| 3: | " | over 30 % | |
| 2: | " | below 30 % | |
| 1: | " | below 10 % | |
| 0: | " | 0 % | (no phytotoxicity) |

The results are given in Table 2.
(The term "a 1/5000 are Wagner pot" means a pot which covers a space of 0.02 m².)

Table 2

Test results against paddy weeds under irrigation conditions with soil-treatment

| Compound No. | Amount of active ingredient (g/10 ares) | Degree of damage | | | Phytotoxicity Rice plant |
|---|---|---|---|---|---|
| | | Barnyard grass | Spikerush | Broad-leaved weed | |
| (1) | 500 | 5 | 5 | 5 | 0 |
| | 250 | 5 | 5 | 5 | 0 |
| | 100 | 5 | 4–5 | 5 | 0 |
| (2) | 500 | 5 | 5 | 5 | 0 |
| | 250 | 5 | 4–5 | 5 | 0 |
| | 100 | 5 | 4 | 4–5 | 0 |
| (3) | 500 | 5 | 5 | 5 | 0 |
| | 250 | 5 | 4–5 | 5 | 0 |
| | 100 | 5 | 4 | 5 | 0 |
| (4) | 500 | 5 | 5 | 5 | 0 |
| | 250 | 5 | 4 | 5 | 0 |
| | 100 | 4 | 3 | 4 | 0 |
| (5) | 500 | 5 | 5 | 5 | 0 |
| | 250 | 5 | 4–5 | 5 | 0 |
| | 100 | 4 | 4 | 4 | 0 |
| (6) | 500 | 5 | 5 | 5 | 0 |
| | 250 | 5 | 5 | 5 | 0 |
| | 100 | 5 | 4–5 | 5 | 0 |
| (7) | 500 | 5 | 5 | 5 | 0 |
| | 250 | 5 | 4 | 5 | 0 |
| | 100 | 5 | 4 | 4 | 0 |
| 8 | 500 | 5 | 5 | 5 | 0 |
| | 250 | 5 | 4 | 5 | 0 |
| | 100 | 4–5 | 3 | 4 | 0 |
| (9) | 500 | 5 | 4–5 | 5 | 0 |
| | 250 | 5 | 4 | 5 | 0 |
| | 100 | 5 | 4 | 4 | 0 |
| (10) | 500 | 5 | 4–5 | 5 | 0 |
| | 250 | 5 | 4 | 5 | 0 |
| | 100 | 4 | 4 | 4–5 | 0 |
| (11) | 500 | 5 | 4 | 4–5 | 0 |
| | 250 | 4–5 | 4 | 4 | 0 |
| | 100 | 4 | 3 | 3 | 0 |
| (12) | 500 | 5 | 4–5 | 5 | 0 |
| | 250 | 5 | 4 | 5 | 0 |
| | 100 | 5 | 4 | 4–5 | 0 |
| (13) | 500 | 5 | 4–5 | 5 | 0 |
| | 250 | 4 | 4 | 4–5 | 0 |
| | 100 | 4 | 3–4 | 4 | 0 |
| (14) | 500 | 5 | 4–5 | 5 | 0 |
| | 250 | 5 | 4 | 5 | 0 |
| | 100 | 4–5 | 4 | 4–5 | 0 |
| (15) | 500 | 5 | 5 | 5 | 0 |
| | 250 | 5 | 4 | 5 | 0 |
| | 100 | 4–5 | 4 | 4–5 | 0 |
| (16) | 500 | 5 | 4 | 5 | 0 |
| | 250 | 5 | 4 | 4–5 | 0 |
| | 100 | 4–5 | 3–4 | 4 | 0 |
| (17) | 500 | 5 | 5 | 5 | 0 |
| | 250 | 5 | 4–5 | 5 | 0 |
| | 100 | 5 | 4 | 4–5 | 0 |
| (18) | 500 | 5 | 4–5 | 5 | 0 |
| | 250 | 5 | 4 | 5 | 0 |
| | 100 | 4–5 | 4 | 4–5 | 0 |
| (19) (Control) | 500 | 5 | 4 | | 0 |
| | 250 | 4–5 | 4 | 4 | 0 |
| | 100 | 4 | 3–4 | 4 | 0 |
| (20) | 500 | 5 | 4–5 | 5 | 0 |
| | 250 | 5 | 4 | 4–5 | 0 |
| | 100 | 4 | 4 | 4 | 0 |
| (21) | 500 | 5 | 4–5 | 5 | 0 |
| | 250 | 5 | 4 | 4–5 | 0 |
| | 100 | 5 | 3 | 4 | 0 |
| (22) | 500 | 5 | 5 | 4–5 | 0 |
| | 250 | 4–5 | 4 | 4 | 0 |
| | 100 | 4 | 3 | 3 | 0 |
| (23) | 500 | 5 | 5 | 5 | 0 |
| | 250 | 4–5 | 4 | 5 | 0 |
| | 100 | 4 | 3–4 | 4–5 | 0 |
| (24) | 500 | 5 | 4 | 4 | 0 |
| | 250 | 4–5 | 4 | 3 | 0 |
| | 100 | 4 | 3–4 | 3 | 0 |
| (25) | 500 | 5 | 4 | 4–5 | 0 |
| | 250 | 4–5 | 3 | 4 | 0 |
| | 100 | 4 | 3 | 3 | 0 |
| (A) (Comparison) | 500 | 5 | 5 | 5 | 0–1 |
| | 250 | 5 | 4 | 3 | 0 |
| | 100 | 3 | 3 | 2 | 0 |
| un-treated | — | 0 | 0 | 0 | 0 |

Table 2-continued

Test results against paddy weeds under irrigation conditions with soil-treatment

| Compound No. | Amount of active ingredient (g/10 ares) | Degree of damage | | | Phytotoxicity Rice plant |
|---|---|---|---|---|---|
| | | Barnyard grass | Spikerush | Broad-leaved weed | |
| (Control) | | | | | |

Notes
1. Broad-leaved weeds: Monochoria, Rotala indica Koehne and False pempernel, etc.
2. Control A: Japanese Pat. Publication No. Sho 43-29024
3. Compound Nos. in the table are the same as in Table 1.

EXAMPLE B

Test against various plants with soil treatment

Test procedure

Seeds of sample plants were sown in a pot of 20 by 30 cm and after 24 hours, the same mixtures as in Example A were sprayed on the soil in amounts of 20, 10, 5, 2.5 and 1.25 kg of active compound per hectare. 3 weeks after spraying, the damage degree was evaluated and classified according to the following standard ranging from 0 to 5 as follows:

0: no effect
1: slight damage or delay in growth
2: marked damage or inhibition of growth
3: heavy damage and only deficient development or only 50% emerged
4: plants partially destroyed after germination or only 25% emerged
5: plants completely dead or not emerged.

The results of the test are given in Table 3.

Table 3

Test results against various plants with soil treatment

| Active Compound | Amount of active compound (kg/ha) | Wheat | Barley | Rice | Cotton | Maize | Cabbage | Barnyard (a) | Common purslane (b) | Goosefoot (c) | Chickweed (d) | Wild amaranth (e) | Finger grass (f) |
|---|---|---|---|---|---|---|---|---|---|---|---|---|---|
| (1) | 20 | 4 | 4 | 4 | 4 | 4 | 4 | 5 | 5 | 5 | 5 | 5 | 5 |
| | 10 | 1–2 | 2 | 1–2 | 2 | 2 | 2 | 5 | 5 | 5 | 5 | 5 | 5 |
| | 5 | 0 | 0 | 0 | 0 | 0 | 0 | 5 | 5 | 5 | 5 | 5 | 5 |
| | 2.5 | 0 | 0 | 0 | 0 | 0 | 0 | 5 | 5 | 5 | 5 | 5 | 5 |
| | 1.25 | 0 | 0 | 0 | 0 | 0 | 0 | 5 | 4–5 | 4–5 | 4 | 4–5 | 4–5 |
| (A) (Comparison) | 20 | 5 | 5 | 5 | 5 | 5 | 5 | 5 | 5 | 5 | 5 | 5 | 5 |
| | 10 | 1–2 | 2 | 3 | 2 | 2 | 1–2 | 5 | 5 | 5 | 5 | 5 | 5 |
| | 5 | 0 | 0 | 0 | 0 | 0 | 0 | 4 | 5 | 5 | 5 | 5 | 5 |
| | 2.5 | 0 | 0 | 0 | 0 | 0 | 0 | 3 | 4 | 4 | 4 | 4 | 3 |
| | 1.25 | 0 | 0 | 0 | 0 | 0 | 0 | 2 | 2 | 2 | 2 | 2 | 2 |

Notes
1. The compound number in the Table corresponds to that of Example (1).
2. (A): French Pat. No. 1328112: Benzyl-N,N-diethylthiolcarbamate
3. (a) Echinochloa (b) Portulacca (c) Chenopodium (d) Stellaria (e) Amaranthus (f) Digitaria

EXAMPLE C

Test against carmine mite (Tetranuchus telarius)
Preparation of the active compound:
Solvent: 3 parts by weight of acetone
Emulsifier: 1 part by weight of alkylaryl polyglycol ether In order to prepare a suitable preparation of the active compound, 1 part by weight of the active compound was mixed with the above amounts of acetone and the emulsifier to prepare an emulsion concentrate. The emulsion concentrate was diluted with water to the desired final concentration.

Testing method:

A kidney bean plant, during the period of the 2nd foliage leaf development, planted in a pot of 6 cm diameter, was inoculated with 50 – 100 adult and young carmine mite and after 2 days, a preparation of the active compound described above was sprayed onto the pot at a rate of 40 ml per pot.

The so-treated pot was investigated to evaluate the controlling effect after allowing to stand at room temperature for 10 days, and the effect was rated on a scale as follows:

3: no living adult and young insects
2: below 5% living insects with respect to the untreated pot
1: 6–50% living insects with respect to the untreated pot
0: over 51% living insects with respect to the untreated pot The average results obtained are shown in the Table 4.

Table 4

Test results against carmine mites

| Compound No. | Concentration of active ingredient (ppm) | | |
|---|---|---|---|
| | 1000 | 300 | 100 |
| (2) | 3 | 2 | 2 |
| (3) | 3 | 3 | 3 |
| (4) | 3 | 2 | 1 |
| (5) | 3 | 2 | 1 |
| (6) | 3 | 2 | 1 |
| (8) | 3 | 3 | 3 |
| (11) | 3 | 3 | 2 |
| (12) | 3 | 3 | 2 |
| (13) | 3 | 2 | 1 |
| (15) | 3 | 2 | 1 |
| (18) | 3 | 2 | 1 |
| (23) | 3 | 3 | 3 |
| (25) | 3 | 2 | 1 |
| Kelthane (commercial comparison) | 3 | 2 | 0 |
| no-treatment (control) | 0 | | |

Notes:
1. The compound Nos. in the Table correspond to those of Table 1.
2. Kelthane: bis(p-chlorophenyl)trichloroethanol.

It will be understood that the specification and examples are illustrative but not limitative of the present invention and that other embodiments within the spirit and scope of the invention will suggest themselves to those skilled in the art.

What is claimed is:

1. Cyclohexyl carbamate compound of the formula:

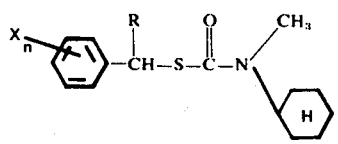

wherein
X is hydrogen and
R is hydrogen or methyl.

2. Compound as claimed in claim 1 wherein said compound is designated benzyl-N-methyl-N-cyclohexylthiolcarbamate.

3. Compound as claimed in claim 1 wherein said compound is designated α-methylbenzyl-N-methyl-N-cyclohexylthiolcarbamate.

* * * * *